(12) United States Patent
Eberheim et al.

(10) Patent No.: US 8,558,557 B2
(45) Date of Patent: Oct. 15, 2013

(54) INDUCTIVE CONDUCTIVITY MEASUREMENT CELL

(75) Inventors: Andreas Eberheim, Waldheim (DE); Thomas Nagel, Wilsdruff (DE); Andreas Siedler, Ludwigsburg (DE); Marco Völker, Döbeln (DE)

(73) Assignee: Endress + Hauser Conducta Gesellschaft für Mess-und Regeltechnik mbH + Co. KG, Gerlingen (DE)

( * ) Notice: Subject to any disclaimer, the term of this patent is extended or adjusted under 35 U.S.C. 154(b) by 467 days.

(21) Appl. No.: 12/733,047

(22) PCT Filed: Aug. 8, 2008

(86) PCT No.: PCT/EP2008/060426
§ 371 (c)(1),
(2), (4) Date: Apr. 22, 2010

(87) PCT Pub. No.: WO2009/024479
PCT Pub. Date: Feb. 26, 2009

(65) Prior Publication Data
US 2010/0207643 A1 Aug. 19, 2010

(30) Foreign Application Priority Data
Aug. 17, 2007 (DE) .......................... 10 2007 039 015

(51) Int. Cl.
*G01R 27/28* (2006.01)
(52) U.S. Cl.
USPC ........................................................ 324/654
(58) Field of Classification Search
USPC ........................................................ 324/654
See application file for complete search history.

(56) References Cited

U.S. PATENT DOCUMENTS

| | | | |
|---|---|---|---|
| 3,054,946 A | | 9/1962 | Esterson |
| 3,404,335 A | | 10/1968 | Kidder |
| 3,564,400 A | * | 2/1971 | Pike et al. ...................... 324/306 |
| 5,160,893 A | * | 11/1992 | Lamson ........................ 324/654 |
| 5,252,925 A | | 10/1993 | Matsumoto |
| 5,680,051 A | * | 10/1997 | Wakamatsu .................. 324/445 |
| 5,793,214 A | | 8/1998 | Wakamatsu |
| 7,279,903 B2 | * | 10/2007 | Quackenbush et al. ........ 324/445 |
| 2006/0249729 A1 | * | 11/2006 | Mundt et al. .................... 257/48 |
| 2007/0008060 A1 | * | 1/2007 | Weller et al. .................. 336/229 |

FOREIGN PATENT DOCUMENTS

| | | |
|---|---|---|
| DE | 1 598 074 | 7/1970 |
| DE | 41 16 468 | 11/1992 |
| WO | WO 2007/135035 | 11/2007 |

* cited by examiner

*Primary Examiner* — Jeff Natalini
(74) *Attorney, Agent, or Firm* — Bacon & Thomas, PLLC

(57) ABSTRACT

An inductive conductivity measurement cell of the invention includes: sending coil, a receiving coil, and a coil support body having an annular, sending coil chamber and an annular, receiving coil chamber, wherein there extends through the coil support body at least one section of a closed media path, which passes through the sending coil chamber and through the receiving coil chamber, characterized in that the coil support body has first connection bores, which extend from a surface of the coil support body to the sending coil chamber and through which the connection lines of the sending coil extend, and second connection bores, which extend from a surface of the coil support body to the receiving coil chamber and through which the connection lines of the receiving coil extend. The connection lines of the sending coil in the first connection bores are shielded from the connection lines of the receiving coil in the second connection bores by the coil support body.

12 Claims, 2 Drawing Sheets

INDUCTIVE CONDUCTIVITY MEASUREMENT CELL

TECHNICAL FIELD

The present invention relates to an inductive conductivity measurement cell for determining the conductivity of a liquid medium, in which the conductivity measurement cell is immersed in the medium.

BACKGROUND DISCUSSION

Such an inductive conductivity measurement cell includes, usually, a sending coil, a receiving coil, and a coil support body having an annular, sending coil chamber and an annular, receiving coil chamber, wherein there extends through the coil support body at least a section of a closed media path, which passes through the sending coil chamber and through the receiving coil chamber. As is known to those skilled in the art, an inductive conductivity measurement cell can be described as a combination of two transformers, wherein the closed media path acts as a winding of both transformers. By evaluation of the signal of a receiving coil in the receiving coil chamber in response to the signal of a sending coil in the sending coil chamber, consequently, the conductivity of the medium in the closed media path can be ascertained.

The measuring range of inductive conductivity sensors is, however, limited, especially toward low conductivities, by direct couplings between the sending coil and the receiving coil independently of the measured medium, as will briefly be explained on the basis of an example from the state of the art.

FIGS. 3 and 4 show a perspective view and a sectional view through a coil support body of the state of the art. The coil support body has an annular, sending coil chamber 112 and an annular, receiving coil chamber 114, which are separated from one another by a central, annular partition 119. A corresponding conductivity sensor is available from Endress+Hauser under the designation CLS54.

The grounded coil support body is manufactured of metal and largely shields the coils from one another. However, there is in a mounting area 120 a relatively large bore 122, through which connection lines for the sending coil, on the one hand, and the receiving coil, on the other hand, are led into the sending coil chamber 112 and into the receiving coil chamber 114.

This bore 122 represents a passageway between the sending coil chamber and the receiving coil chamber, whereby a residual coupling between the sending coil and the receiving coil arises, which is independent of the measured medium and, insofar, limits the conductivity measurement range downwards.

SUMMARY OF THE INVENTION

It is, therefore, an object of the present invention to provide an inductive conductivity measurement cell, which overcomes the disadvantages of the state of the art.

The object is achieved according to the invention by the conductivity measurement cell which includes at least one sending coil, at least one receiving coil, and a coil support body having an annular, sending coil chamber and an annular, receiving coil chamber, wherein there extends through the coil support body at least a section of a closed media path, which passes through the sending coil chamber and through the receiving coil chamber, characterized in that the coil support body has first connection bores, which extend from a surface of the coil support body to the sending coil chamber and through which the connection lines of the sending coil extend, and second connection bores, which extend from a surface of the coil support body to the receiving coil chamber and through which the connection lines of the receiving coil extend, wherein the connection lines of the sending coil in the first connection bores are shielded from the connection lines of the receiving coil in the second connection bores by the coil support body.

In a currently preferred embodiment of the invention, the functions of sending coil and receiving coil solid are assigned, i.e., a sending coil is always a sending coil and a receiving coil is always a receiving coil. The invention includes, however, also embodiments, in the case of which the functions can be assigned variably. However, also in the case of these embodiments, in each actual measured value registering, a coil is assigned a specific function, so that at least one coil serves as sending coil and at least one other as receiving coil.

In a currently preferred embodiment of the invention, the surface of the coil support body has a mounting area, from which the first and second connection bores extend to their respective coil chambers, and wherein the mounting area has a receiving slot for an end section of a circuit board. Preferably, the receiving slot isolates the first connection bores from the second connection bores.

The connection bores have according to a further development of the invention a ratio of diameter to length of no more than 1:4, preferably no more than 1:6.

The sending coil chamber and the receiving coil chamber are arranged coaxially in a first embodiment of the invention.

In a second embodiment, the sending coil chamber and the receiving coil chamber are arranged coplanarly and with parallel axes.

The annular coil chambers have, in each case, a surrounding inner wall and a surrounding outer wall, as well as an annular end wall, which extends between the annular inner wall and the annular outer wall. The annular inner wall surrounds an opening, through which a section of the media path extends.

Insofar as the coil support body has a conductive material, especially a metal material, the sending coil and the receiving coil in the coil chambers are shielded from one another by the coil support body.

In the coaxial embodiment of the coil chambers, the annular end walls of the coil chambers are facing one another. In a further development of this embodiment, the two end walls are embodied as a shared partition between the sending coil chamber and the receiving coil chamber.

Apart from the connection bores for the coils, the sending coil chamber and the receiving coil chamber preferably have no additional perforations.

The sending coil and the receiving coil are preferably wound each on its own toroidal core.

Furthermore, for reducing capacitive couplings and/or magnetic couplings between the sending coil and the receiving coil, electrostatic shieldings, or magnetic shieldings, can be provided.

For the magnetic shielding, the toroidal coils can, for example, in each case, be provided with a magnetically highly permeable jacketing, which has an annular, surrounding gap, in order to prevent an eddy current path. Preferably, the edge regions of the jacketing overlap by at least one separation, preferably by at least two separations, between the edge regions in the region of the gap, in order to configure the magnetic shielding as effectively as possible.

For electrostatic shielding, at least, in each case, the frontside opening of the coil chambers lying opposite the annular end wall can be covered with a shielding sheet, or a shielding foil, for example, a copper foil. Equally, the toroidal coil can be provided with a corresponding jacketing, wherein, in each case, a annular, surrounding gap is to be provided for preventing eddy currents. Preferably, the edge regions of the jacketing overlap by at least one separation, preferably by at least two separations between the edge regions in the region of the gap, in order to make the electrostatic shielding as effective as possible. A corresponding overlap is preferably provided between a covering and the coil support body, wherein a galvanic coupling is to be provided between the covering and the coil support body.

The coil support body lies, according to a currently preferred embodiment of the invention, at the ground of an exciter circuit for the driving the sending coil, or at the ground of an evaluating circuit for the evaluation of the signals of the receiving coil. Preferably, the two circuits have the same ground.

BRIEF DESCRIPTION OF THE DRAWINGS

The invention will now be explained on the basis of an example of an embodiment illustrated in the drawing, the figures of which show as follows.

DETAILED DISCUSSION IN CONJUNCTION WITH THE FIGS. 1 AND 2

Figure 1:
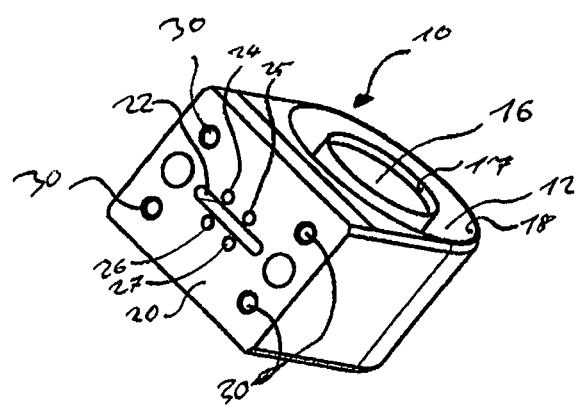
FIG. 1 is a perspective view of a coil support body of an inductive conductivity measurement cell of the invention.
Figure 2:
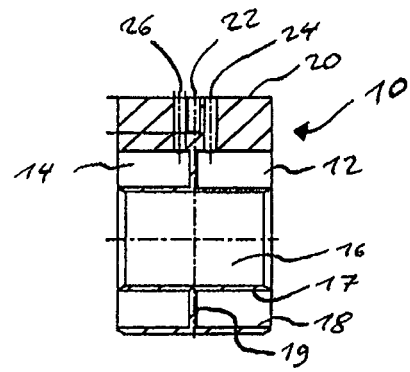
FIG. 2 is a longitudinal section through the coil support body of FIG. 1.
Figure 3:
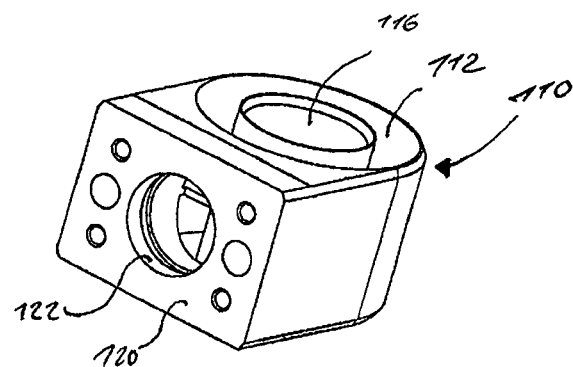
FIG. 3 is a perspective view of a coil support body of the state of the art.
Figure 4:
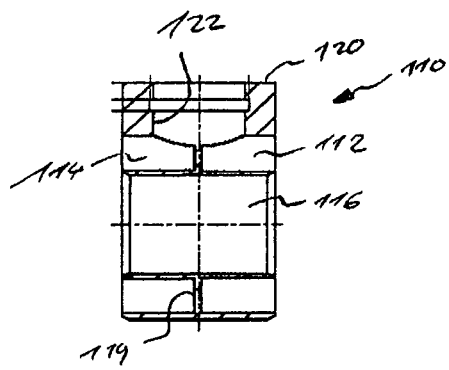
FIG. 4 is a longitudinal section through the coil support body of FIG. 3.

The coil support body 10 of a conductivity sensor of the invention shown in FIGS. 1 and 2 includes two annular coil chambers in coaxial arrangement, namely the sending coil chamber 12 and the receiving coil chamber 14. The coil chambers are bounded by an inner cylindrical wall 17, an outer cylindrical wall 18 and an annular partition 19 extending essentially perpendicularly to the cylinder axis between the sending coil chamber 12 and the receiving coil chamber 14. The described arrangement of the chambers of a coil support body can be achieved, for example, by milling from a metal body, for example, an aluminum body, or by manufacturing as a metal casting. Equally, a plastic, molded part can be manufactured, which is then coated with metal.

For power supply of the sending coil in the sending coil chamber 12, bores 24 and 25 extend from a mounting area 20 into the sending coil chamber, wherein the bores have a very small diameter relative to their length. Corresponding bores 26 and 27 are provided for leading connection lines into the receiving coil chamber 14 for the receiving coil.

Milled into the mounting area 20 between the connection bores 24 and 25 for the sending coil, on the one hand, and the connection bores 26 and 27 for the receiving coil, on the other hand, is a slot 22, into which an end section of a circuit board can be introduced, so that the circuit board protrudes out from the mounting area perpendicularly to the plane thereof, and separates from one another the connection lines of the two coils led out of the coil support. Slot 22 does not extend all the way through the wall of the coil support. The signals of the receiving coil can be fed on the circuit board directly after the passage of the connection lines through the bores 26 and 27 to a signal conditioning circuit. Correspondingly, on the other side of the circuit board, an output of a driver circuit for driving the sending coil can be positioned in the direct vicinity of the openings of the connection bores 24 and 25. Insofar as the coil support body of the inductive conductivity measurement cell of the invention has no perforations placing the coil chambers in communication with one another, degrading of the measuring by cross couplings between the exciter signal to the receiving coil is significantly reduced compared with inductive conductivity measurement cells of the state of the art.

The invention claimed is:

1. An inductive conductivity measurement cell, comprising:
   at least one sending coil;
   at least one receiving coil; and
   a coil support body having an annular, sending coil chamber and an annular, receiving coil chamber, wherein:
   there extends through said coil support body at least a section of a closed, media path, which passes through said at least one sending coil chamber and through said receiving coil chamber;
   said coil support body has first connection bores, which extend from a surface of said coil support body to said sending coil chamber and through which connection lines of said at least one sending coil extend, and second connection bores, which extend from said surface of said coil support body to said receiving coil chamber and through which the connection lines of said receiving coil extend;
   the connection lines of said at least one sending coil in said first connection bores are shielded from the connection lines of said receiving coil in said second connection bores by said coil support body;
   said surface is a mounting area, from which the first and second connection bores extend to their respective coil chambers;
   the mounting area has a receiving slot for an end section of a circuit board;
   said receiving slot isolates the first connection bores from the second connection bores; and
   said circuit board is introduced into said receiving slot;
   said connection line of said sending coil is fed to a first side of said circuit board; and
   said connection line of said receiving coil is fed to a second side of said circuit board.

2. The inductive conductivity measurement cell as claimed in claim 1, wherein:
   the connection bores have a ratio of diameter to length of no more than 1:4.

3. The inductive conductivity measurement cell as claimed in claim 1, wherein:
   said at least one sending coil chamber and said receiving coil chamber are coaxially arranged.

4. The inductive conductivity measurement cell as claimed in claim 1, wherein:
   said at least one sending coil chamber and said receiving coil chamber are arranged axially parallelly and coplanarly.

5. The inductive conductivity measurement cell as claimed in claim 1, wherein:
   said annular coil chambers each have a surrounding inner wall and a surrounding outer wall, as well as an annular end wall, which extends between said annular inner wall and said annular outer wall; and
   said annular inner wall surrounds an opening, through which a section of the media path extends.

6. The inductive conductivity measurement cell as claimed in claim 5, wherein:
said annular end walls of said coil chambers are embodied facing one another, or as a shared partition between said sending coil chamber and said receiving coil chamber.

7. The inductive conductivity measurement cell as claimed in claim 1, wherein:
said at least one sending coil chamber and said receiving coil chamber, except for the connection bores for the coils, have no additional perforations.

8. The inductive conductivity measurement cell as claimed in claim 1, wherein:
said at least one sending coil and said receiving coil each have a toroidal core.

9. The inductive conductivity measurement cell as claimed in claim 8, wherein:
said toroidal coils are each provided with a magnetically highly permeable jacketing, which has an annularly surrounding gap.

10. The inductive conductivity measurement cell as claimed in claim 1, wherein:
for reducing capacitive couplings between said at least one sending coil and said receiving coil, an electrostatic shielding is provided in the region of an end opening of at least one coil chamber.

11. The inductive conductivity measurement cell as claimed in claim 1, wherein:
said coil support body comprises one of: metal, a conductive plastic, and a conductive, composite material.

12. The inductive conductivity measurement cell as claimed in claim 1, wherein:
the connection bores have a ratio of diameter to length of no more than 1:5.

* * * * *